United States Patent [19]

Greco

[11] Patent Number: 5,010,202

[45] Date of Patent: Apr. 23, 1991

[54] NOVEL SILICON-ORGANIC COMPOUNDS, CONTAINING AN OXAZOLIDINE GROUP

[75] Inventor: Alberto Greco, Desano, Italy

[73] Assignee: Enichem Synthesis S. p. A., Palermo, Italy

[21] Appl. No.: 522,218

[22] Filed: May 11, 1990

[30] Foreign Application Priority Data

May 11, 1989 [IT] Italy .............................. 20442 A/89

[51] Int. Cl.$^5$ .......................... C07D 263/04; C07F 7/02
[52] U.S. Cl. ........................................ 548/110; 546/14; 540/4
[58] Field of Search ............... 548/110; 546/14; 540/4

Primary Examiner—Mary C. Lee
Assistant Examiner—Joseph K. McKane
Attorney, Agent, or Firm—Hedman, Gibson, Costigan & Hoare

[57] ABSTRACT

Novel silicon-organic compounds containing an oxazolidine group are defined by the general formula (I):

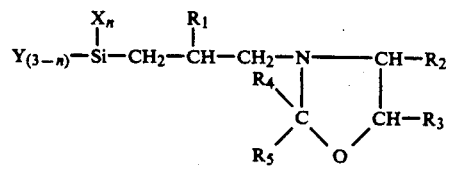

wherein $R_1$, $R_2$, $R_3$, $R_4$, $R_5$, X, n and y have the meanings reported in the description. These compounds are capable of co-cross-linking and to act as adhesion promoters on various polar substrates, in compositions based on poly-isocyanates, polyepoxides or polacrylates, in the field of sealants and adhesives.

5 Claims, No Drawings

NOVEL SILICON-ORGANIC COMPOUNDS, CONTAINING AN OXAZOLIDINE GROUP

This invention relates to silicon-organic compounds which contain an oxazolidine nucleus and a silicon atom bonded to at least one hydrolytically labile group, and relates also to the preparation of such compounds and their quite particular use as adhesion-promoters and also as cross-linking adjuvants for systems capable of hardening under the effect of moisture, based on poly-isocyanates, acrylate polymers and polyepoxides in compositions for sealing and adhesive coatings.

The use of polyoxazolidines as cross-linking systems and hardeners in paints or sealants, above all based on poly-isocyanates is well known in the patent literature. U.S. Pat. Nos. 3,743,626 and 4,138,545 disclose the use of a few polyoxazolidines as hardeners in "single-component" compositions based on poly-isocyanates, both aliphatic and aromatic. As disclosed in the patents cited now, polyoxazolidines are obtained by a transesterification reaction between a hydroxyethyloxazolidine (A) and esters of carboxylic, or polycarboxylic acids:

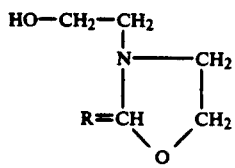 (A)

or by reacting a glycol, or a polyol, with an oxazolidine (B).

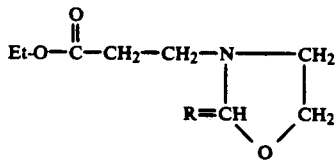 (B)

In the BE-A-865 893, polyoxazolidines are obtained by causing poly(di)isocyanates to react with two (or more) mols of hydroxyethyloxazolidine (A).

The same reference discloses the employment of these compounds as cross-linking adjuvants in the presence of poly-isocyanate based systems of the monocomponent moisture-hardening type, and are intended to be used as sealants.

Other types of polyoxazolidine for a similar use are disclosed in EP-A-0 288 935.

All the examples referred to above show systems in which the oxazolidine reacts "of its own" without the intervention of any additional different reactive group other than the one with which it just interacts, such as the isocyanate group.

As a matter of fact, the hydrolytically labile oxazolidine group, in the presence of moisture, becomes rapidly hydrolyzed to give alkanolamines and aldehydes, or ketones. Therefore, oxazolidines, once they have been hydrolyzed, are capable of co-reacting with a host of reactive substrates, such as polyisocyanates, polyepoxides or acrylates (Michael addition); more particularly, oxazolidines are outstandingly appreciated in the polyisocyanate-based formulation of the moisture-hardening, single-component type, since they are not basic enough to have a significant action upon the "post-life" of the compositions concerned, while concurrently possessing a reactivity which is sufficient to enable them to be hydrolyzed in the presence of moisture, even under the merely environmental conditions, and to supply reactive groups capable of cross-linking the polyisocyanate-based systems quickly.

The silicon-organic compounds, which are generally used as coupling agents, are known in the art.

They contain, as a rule, besides the group (C)

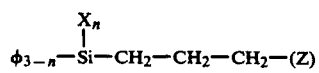

wherein $\phi$ is a hydrolytically labile group of the alkoxy, aminoxy, acyloxy type or another like group, a second functional group (Z) of the kind $-NH_2$, $-NH-CH_2-CH_2-NH_2$, $-SH$,

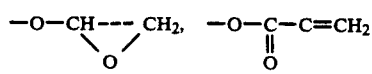

Among them, a few are reactive relative to the isocyanate-based systems (Z is $-NH_2$, $-NH-CH_2-CH_2-NH_2$, $-SH$), whereas others are not such, at least in the absence of a catalyst and under environmental conditions

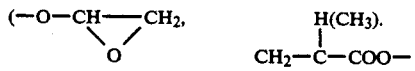

The systems which are capable of reacting with poly-isocyanates (which contain the $-NH_2$ group, or $-NH-CH_2-CH_2-NH$, or $-SH$) have, however, a restricted field of use, since the formation of ureic or thiocarbamic groups originates increases, which are sometimes imposing, of the viscosity, and such as to reduce, of necessity, their quantity in the compositions in which they are blended.

The advantage of using sealing and/or thermosetting compositions containing the groups

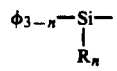

is nonetheless worth noting, because the hydrolysis of the silicon-containing groups in the presence of the environmental humidity is conducive to silanols which are in a position to exalt the interfacial bonds between a polymer and the substrates of a polar character, thereby improving the properties of the adhesive and the sealants.

It would, however, be desirable to have, in the polyurethan chemistry, coupling agents available, which would be reactive in the environment in which they are incorporated and moreover such as not to destabilize the formulations concerned while improving the adhesive power.

An objective of the present invention is to provide a class of compounds fulfilling the requirements outlined above and capable of improving the adhesive power of the systems in which they are incorporated, thus matching the appreciable properties of the oxazolidine group with those of the silicon function which is proper of the coupling agents.

In accordance with the foregoing, and according to a first aspect, the present invention relates to novel compounds, which can be defined by the general formula (I):

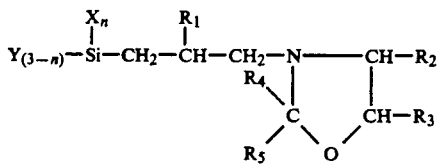

wherein n is an integer from 0 to 2, X is a hydrogen atom, a linear-, or a branched-chain alkyl, or an aryl, y is a hydrolytically labile organic group selected from the groups:

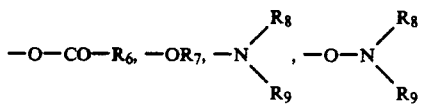

wherein
$R_6$, $R_7$, $R_8$, $R_9$ as specified hereunder;
$R_1$ is a hydrogen atom or a methyl;
$R_2$ and $R_3$, equal to, or different from one another, are a hydrogen atom, a linear- or a branched-chain alkyl containing from 1 to 6 carbon atoms, or an aryl;
$R_4$ and $R_5$, equal to, or different from one another, are a hydrogen atom, a linear- or a branched-chain alkyl or alkenyl containing from 1 to 6 carbon atoms, a cycloalkyl, an aryl, or $R_4$ and $R_5$, taken simultaneously together with the carbon atom to which they are bonded, make up a cycloaliphatic ring having from 4 to 8 carbon atoms;
$R_6$ and $R_7$, equal to, or different from one another, are an alkyl or an alkenyl having from 1 to 6 carbon atoms;
$R_8$ and $R_9$, equal to, or different from one another, are an alkyl, or an alkenyl having from 1 to 6 carbon atoms, a cycloalkyl, an aryl, or $R_8$ and $R_9$, considered conjointly together with the adjacent nitrogen atom, represent a saturated 5-membered, 6-membered, 7-membered, or 8-membered heterocyclic ring.

In the preferred embodiment, y is a methoxy or an ethoxy radical; X, if present, is (with n equal to 1 or 2) a methyl, $R_1$, $R_2$, $R_3$, and $R_4$ are a hydrogen atom, whereas $R_5$ is a linear- or a branched-chain alkyl having from 1 to 6 carbon atoms.

A particular and nonlimiting example of a preferred compound for the purposes of the present invention is the compound (II):

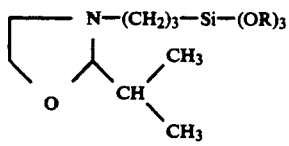

wherein R is an ethyl or a methyl.

Correspondingly, nonlimiting preferred examples of compounds for the purposes of the present invention, containing 2 or 3 hydrolytically unstable silicon bonds, are the compounds (III) and (IV), respectively:

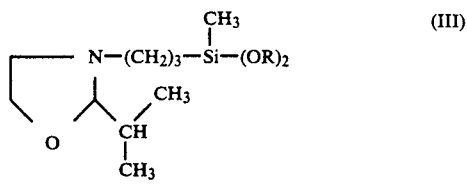

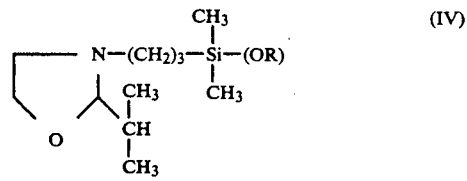

wherein R has the meaning specified hereinabove.

The oxazolidine compounds of the present invention are readily obtained by reacting a (meth)allyloxazolidine (V)

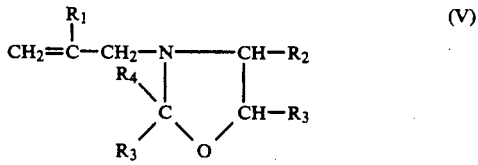

wherein the substituents $R_1$, $R_2$, $R_3$, $R_4$, and $R_5$ have the above referred to meanings, with a silane having the formula (VI):

wherein X, y and n have the meanings referred to above. The reaction, which takes place by involving the SI-H bonds of (VI), is carried out preferentially with the reactants taken in stoichiometric proportions.

The preferably used silanes are:

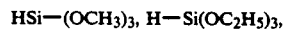

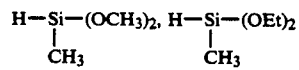

Generally, the reaction proceeds very smoothly with heat build-up up to high conversion ratings, desirably in the presence of catalysts and at a temperature comprised from 50° C. to 150° C., preferably at a temperature comprised from 80° C. to 120° C.

Reactional catalysts are metallic platinum, the complexes of rhodium, palladium or other transition metals, such as hexachloroplatinic acid ($H_2PtCl_6$) or radicalic initiators, such as azobisisobutyronitrile.

The amounts of catalysts are considerably different and are strictly bound to the type of catalytic system adopted.

In the case of catalysts of the radicalic type, the amounts may vary from 0.01% to 5%, by weight, and preferably from 1% to 5%, by weight, relative to the reactants.

Conversely, in the case of metallic catalysts, (Rh, Pd, Pt and the like) and their compounds, the catalytic amounts used are really low and generally range from 1 part to 100 part per million (ppm) relative to the reactants, and preferably from 1 ppm to 10 ppm.

Whenever acidic catalyst are used, such as hexachloroplatinic acid, it is advisable to introduce, in the reaction medium, small values of a protonic acceptor, such as glycidol, or trimethylorthoformate, to reduce the acidity of the system, towards which the oxazolidinic molecule is extremely sensitive.

It is not imperative to work under pressure, but the reaction can be carried out also in an autoclave, if so desired it is possible to conduct the reaction either in bulk, or in the presence of inert solvents as well.

The use of an inert solvent encourages the dissipation and the control of the reaction heat.

Inert solvents are all those solvents which do not interact with the $\equiv$Si—H function and the hydrocarbons, both aliphatic and aromatic, belong to this class, together with the linear cyclic ethers and others.

If the reaction is carried out in a solvent-less environment, the control of the hexothermal reaction can be conveniently made by a portionwise addition (dripping) of the (meth)allyloxazolidine (V) component to the reaction medium.

No matter how the reaction is carried out, either in the presence of solvents or in their absence, there is observed, within the above mentioned temperature range, a substantial completion of the reaction in a time which generally does not exceed 6 hours, and is generally from 2 to 6 hours.

The progress of the reaction is monitored spectroscopically, by checking the decrease of the band of the Si—H group in the InfraRed, or of the band of the allyl unsaturations of the (meth)allyloxazolidine.

If a solvent is present, the latter is removed on completion of the reaction by vacuum evaporation.

The yield of the reaction is virtually total and, apart from distilling off the solvent, the as obtained products can be used as such, or purified by a distillation in a reduced vacuum.

The (meth)allyloxazolidines of the general formula (V) can be prepared, in their turn, according to the method described in a copending Italian Patent Application filed in the name of the same Applicants.

This method is reported herein to the only purpose of completing the description of the invention the subject of the present application. More particularly, a (meth)allylamine (M) is caused to react with an alkylene oxide (N) to give a (meth)allylalkanolamine (O):

$$CH_2=\overset{R_1}{\underset{|}{C}}-CH_2-NH_2 +$$

(M)

$$\overset{R_2}{\underset{|}{CH}}\underset{\diagdown O \diagup}{-}\overset{R_3}{\underset{|}{CH}} \quad CH_2=\overset{R}{\underset{|}{C}}-CH_2-NH-\overset{R_2}{\underset{|}{CH}}-\overset{R_3}{\underset{|}{CH}}-OH$$

(N)  (O)

wherein $R_1$, $R_2$ and $R_3$ have the already defined meanings. The reaction is hexothermic, and proceeds smoothly at a temperature of from 0° C. to 120° C., while working with an A-to-B molar ratio from 2 to 10.

The N-methallylalkanolamine (O) is then caused to interact with the aldehyde or the ketone (P) to give the final (meth)allyloxazolidine:

$$CH_2=\overset{R}{\underset{|}{C}}-CH_2-NH-\overset{R}{\underset{|}{CH}}-\overset{R}{\underset{|}{CH}}-OH + \overset{R}{\underset{R}{\diagdown}}C=O \longrightarrow (V)$$

(O)  (P)

The reaction is best carried out at a temperature of from 20° C. to 100° C. in the absence of solvents, by refluxing the aldehyde or the ketone so as azeotropically to remove the water which is being formed as a reaction by-product. The silane compounds which contain SI—H bonds of formula (VI) are well known in the patent and the technical literature.

The process for preparing the compounds (I) of the present invention affords the advantage of giving high yields and a high selectivity for the reactions involved therein.

Moreover, the compounds (I) are products which are compatible with the most common classes of organic polymers, with the concurrent advantage of being fluids having a comparatively low viscosity.

The products having the structure (I) and, more particularly, the structures (II), (III) and (IV) are useful for isocyanate-based formulations in which its is desired to improve the adhesive power, especially towards the substrates which exhibit the more pronounced polar character.

Although the preferred compositions are those which relate to poly-isocyanate-based adhesives and sealants, the silicon-organic compounds of formula (I), due to their reactivity, can find a use in the field of the epoxy resins and the acrylate polymers. As a matter of fact, the characteristics of the oxazolidine system are such that they do not impair the viscosity, or the "pot stability" of the formulations in which the oxazolidine compounds are incorporated, and these oxazolidine compounds ideal partners for moisture-hardening systems of the single-component type. The proportions in which the compounds claimed herein are efficiently incorporated in the formulations, more particularly the adhesives, range from 0.1% to 5%, preferably from 0.2% to 3%: by synthetic formulations, any composition is intended herein, which comprises, in addition to the reactive organic polymers (poly-isocyanates, polyepoxy resins, acrylates or their blends), also inert fillers, both organic and inorganic, plasticizers and other optional additives such as antioxidants, flame-retarders and the like.

The ensuing Examples, which have the only purpose of describing the invention in more detail, are not to be construed, anyway, as a limitation of the scope of this invention.

EXAMPLE 1

Preparation of (IIa)

$$\begin{array}{c} \text{N}-(CH_2)_3-Si-(OCH_3)_3 \\ \diagdown \quad \diagup CH_3 \\ O \quad CH \\ \diagdown CH_3 \end{array}$$

A 50 cm³ flask, equipped with a magnetic bar stirrer, dropping funnel, thermometer and reflux condenser, is charged, under a dry nitrogen blanket, with 0.2 cm³ of trimethyl orthoformate, 15.5 g (0.1 mol) of 2-isopropyl- N-allyl-1,3-oxazolidine, and 10 microliters of a 30% solution (by weight) of $H_2PtCl_6.6H_2O$ in isopropanol.

The reactants are heated, with stirring, on an oil-bath, to an internal temperature of 115° C.

Through the dropping funnel, there is dripped 0.1 mol (12.2 g) of trimethoxysilane, the addition being incrementally made during 30 min approximately.

On completion of the addition, the reaction is allowed to proceed during 3 hours at +120° C.; as that time has elapsed, the Infra Red spectrum showed only a very slight presence of the Si—H band at 2160 cm$^{-1}$.

The distillation under vacuum (0.6665 hPa=0.5 Torr) of the product formed the following heavy fractions: 4.2 g of a fraction having a boiling point of 38° C.-105° C.; 10.8 g of a fraction having a boiling point of 105° C.-110° C., plus a boiler residue of 5.2 g.

The 4.2 g fraction was identified as a non-silylated oxazolidine predominantly, together with a small amount of the second fraction, which was found to be virtually pure (IIa) (yield 41% relative to oxazolidine).

Elemental analysis: For $C_{12}H_{27}NO_3Si$: Theoretical C=55.17%; H=10.34%; N=5.36%; mol. wt. 261. Found C=55.38%; H=10.52%; N=5.25%.

The $^1$H NMR spectrum (250 MHz, CDCl$_3$, TMS as standard)

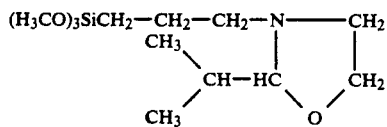

contained signals at 0.65 ppm (2H, Si—CH$_2$); 1.6 ppm (2+1H, Si—CH$_2$—CH$_2$, and N—CH , CH$_3$—CH—CH$_3$)

2,57 ppm (2H, $\diagdown$Si CH$_2$—CH$_2$—CH$_2$);

0,9 ppm (6H, CH$_3$, 3,82 ppm (9H—Si(OCH$_3$)$_3$);
—CH
|
CH$_3$ 2,3 and 3,15 ppm (1+1H, N—C—H)
                        |  |
                        H  CH$_2$

EXAMPLE 2

Preparation of (IIb)

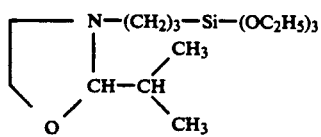

The preparation of Example 1 has been repeated by replacing the trimethoxy silane by the triethoxysilane (0.1 mol, 16.4 g). The vacuum (0.6665 hPa, 0.5 Torr) distillations of the product thus obtained gave the following heavy fractions:

4.8 g of a fraction having a boiling point of from 44° C. to 140° C.;

14.8 g of a fraction having a boiling point of from 140° C. to 148° C., plus about 4 g of a residue.

The fraction having the boiling point range of from 44° C. to 140° C. was predominantly composed of non-silylated oxazolidine (boiling point 40° C.-50° C.), whereas the main fraction consisted of virtually pure IIb (48% yield relative to oxazolidine).

Elemental analysis for $C_{15}H_3NO_3Si$: C=59.41%; H=10.89%; N=4.62% mol. wt. 303 Found: C=59.7%; H=11.0%; N=4.55%.

$^1$H NMR spectrum (conditions as in Example 1):

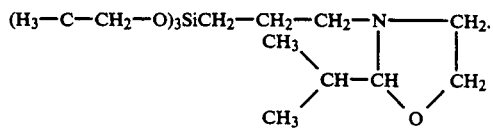

signals at 0.65 ppm (2H, SiCH$_2$—); 1.6 ppm (2+1H, SiCH$_2$—CH$_2$—CH$_2$ and

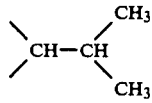

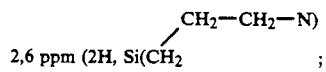

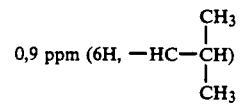

1,20 ppm [9H, Si(—OCH$_2$—CH$_3$)$_3$] 3,85 ppm (6 + 2 + 1H,

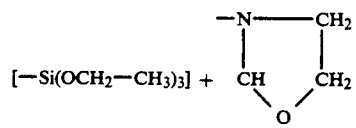

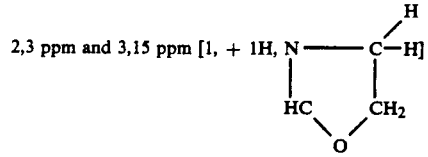

EXAMPLE 3

The preparation was carried out under the same conditions as in Example 1, by replacing the trimethoxysilane by the methyldimethoxysilane.

The distillation under vacuum (0.6665 hPa=0.5 Torr) of the product thus obtained gave the following fractions:

| | | |
|---|---|---|
| 5 g | b.p. | from 40° C. to 85° C. |
| 3,5 g | | from 85° C. to 88° C. |
| 1,5 g | | from 88° C. to 100° C. |
| 6,8 g | | from 100° C. to 105° C. | the first fraction (b.p. range 40° C.-85° C.) was composed of a nonsilylated oxazolidine, the second fraction predominantly consisted of an isomer of (IIIa), in which the oxazolidine proved to be silylated in the internal position (IIIb structure):

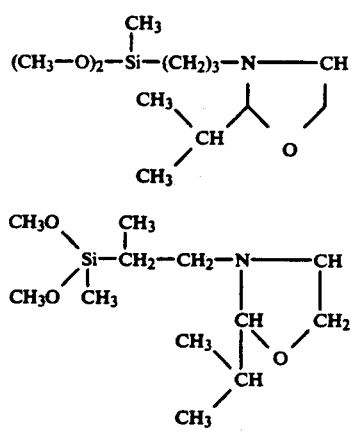

the third fraction (b.p. range 88° C.-100° C.) was composed of a mixture of IIIa and IIIb, whereas the fourth fraction (b.p. range 100° C.-105° C.) consisted of the virtually pure product (IIIa) (Yield 48% of the two isomers relative to the oxazolidine).

Elemental analysis for $C_{12}H_{27}NO_2$: C=58.77%; H=11.02%; N=5.71% mol. wt. 245 Found: C=58.10%; H=11.35%; N=5.63%.

EXAMPLE 4

Application in a polyisocyanate-based formulation of one of the products claimed above for improving adhesion.

A sealing composition was prepared as follows: 92.5 g (50 millimol) of Ravecarb 107 (a polycarbonate diol of an aliphatic nature, Mn 1850, fluid at room temperature and produced by Enichem Syntesis S.p.A.) was reacted with 22.4 g (100.1 millimol) of isophorone diisocyanate at 75° C. during 8 hours until the hydroxyl band faded away in the InfraRed spectrum.

The product was supplemented with 8.2 g (17 millimol) of a polyoxazolidine, of the kind described in BE-A-833 821, the latter being prepared by reacting hexamethylene diisocyanate with hydroxyethyloxazolidine, said polyoxazolidine having the formula:

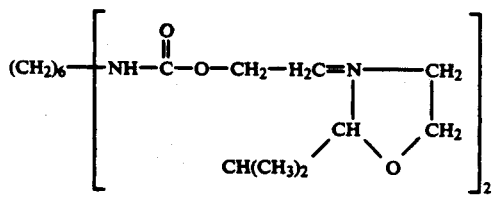

and also 0.7 g (2.7 millimol) of the product (IIa) was added.

The product thus obtained was spread with a knife on a glass plate, to obtain a 0.5 mm-thick layer, and was allowed to cross-link under these conditions for 10 days at ambient temperature and under controlled humidity (23° C., 50% rel. humidity).

An identical sample was prepared and allowed to cross-link under the same conditions, but without adding any (IIa).

After 10 days it was attempted to unstick the two samples from the glass substrate.

It was not possible to unstick the sample formulated with the product (IIa), while it was quite possible to unstick the untreated product.

I claim:

1. Silicon-organic compounds having the general formula (I):

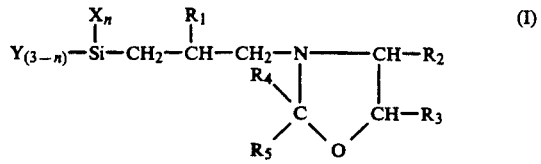

wherein n is an integer from 0 to 2, X is a hydrogen atom, a linear- or a branched-chain alkyl, or an aryl, y is a hydrolytically labile organic group selected from the groups:

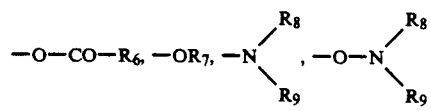

$R_1$ is a hydrogen atom or a methyl, $R_2$ and $R_3$, equal to, or different from one another, are a hydrogen atom, a linear- or a branched-chain alkyl having from 1 to 6 carbon atoms, or an aryl; $R_4$ and $R_5$, equal to, or different from one another, are a hydrogen atom, a linear- or branched-chain alkyl or alkenyl containing from 1 to 6 carbon atoms, a cycloalkyl, an aryl, or $R_4$ and $R_5$, taken concurrently together with the carbon atom and $R_5$, taken concurrently together with the carbon atom to which they are bonded, make up a cycloaliphatic ring having from 4 to 8 carbon atoms; $R_6$ and $R_7$, equal to, or different from one another, are an alkyl or an alkenyl having from 1 to 6 carbon atoms; $R_8$ and $R_9$, equal to, or different from one another, are an alkyl or an alkenyl having from 1 to 6 carbon atoms, a cycloalkyl, an aryl, or $R_8$ and $R_9$, taken concurrently together with the adjacent nitrogen atom, make up a saturated 5-membered, 6-membered, 7-membered or 8-membered heterocyclic ring.

2. A silicon-organic compound of the general formula (I), according to claim 1, wherein y is a methoxy or an ethoxy, and x, if present, (n=1, or 2) is methyl; $R_1$, $R_2$, $R_3$, and $R_4$ are a hydrogen atom, while $R_5$ is a linear- or a branched-chain alkyl having from 1 to 6 carbon atoms.

3. An oxazolidine compound according to claim 1, or 2, consisting of (II):

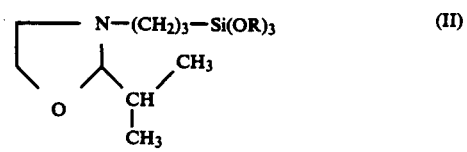

wherein R is a methyl or an ethyl.

4. An oxazolidine compound according to claim 1 or 2, consisting of (III):

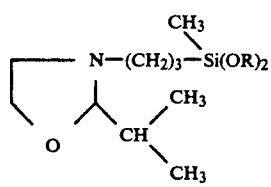
wherein R has the above reported meaning.
5. A silicon-organic compound according to claim 1, 2 or 3, consisting of (IV):
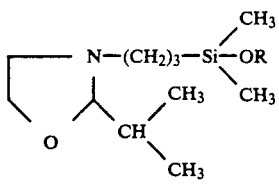
wherein R has the above meaning.
* * * * *